United States Patent [19]

Pfirrmann

[11] 3,963,706

[45] June 15, 1976

[54] SULPHAMOYLPHENYL-IMIDAZOLIDINONES

[75] Inventor: Rolf Wilhelm Pfirrmann, Lucerne, Switzerland

[73] Assignee: Ed. Geistlich Sohne A.G. fur Chemische Industrie, Wolhusen, Switzerland

[22] Filed: Nov. 19, 1973

[21] Appl. No.: 416,854

[30] Foreign Application Priority Data

Nov. 20, 1972 United Kingdom.............. 53437/72

[52] U.S. Cl. ............................................ 260/239.9
[51] Int. Cl.² ...................................... C07D 233/88
[58] Field of Search ................................ 260/239.9

[56] References Cited

UNITED STATES PATENTS 3,284,447   11/1966   Kusuda et al. .................. 260/239.9

*Primary Examiner*—Sam Rosen
*Attorney, Agent, or Firm*—Bacon & Thomas

[57] ABSTRACT

N-Sulphamoylphenyl-substituted imidazolidin-4-ones having useful anti-epileptic activity are prepared by cyclising N-sulphamoylphenyl-substituted α-aminoacetamides with formaldehyde or a reactive derivative of carbonic acid, or by reacting N-halosulphonylphenyl-substituted imidazolidin-4-ones with ammonia.

12 Claims, No Drawings

SULPHAMOYLPHENYL-IMIDAZOLIDINONES

This invention relates to novel compounds of use in the treatment of epilepsy and to processes for their preparation.

In general, the majority of the available antiepileptic drugs are active against either Grand Mal or Petit Mal epilepsy but not against both forms. It has now been found that certain novel sulphamoylphenyl imidazolidinones as described in greater detail hereinafter have shown good activity in both the electro-shock and cardiazol-shock tests, indicative of activity against both Grand and Petit Mal forms of epilepsy, and are considerably better tolerated than other previously proposed imidazoline derivatives.

The term imidazolidinone as used herein includes substituted ring structures and, in particular, imidazolidine-2,4-diones.

According to the present invention there is provided a compound of the general formula

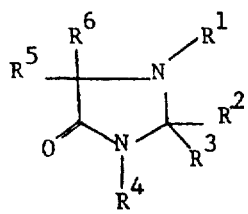

I in which one $R^1$ and $R^4$ represents a sulphamoylphenyl group and the other represents an aryl or cycloaliphatic group; $R^2$ and $R^3$ each represents hydrogen atoms or together represent an oxo group; and $R^5$ and $R^6$, which may be the same or different, represent hydrogen atoms, or aliphatic or cycloaliphatic groups. In particular there is provided a compound of the general formula I in which $R^1$ represents an aryl or cycloaliphatic group and $R^4$ represents a phenyl group, one of $R^1$ and $R^4$ representing a sulphamoylphenyl group;

$R^2$ and $R^3$ each represent hydrogen atoms or together represent an oxo group; and $R^5$ and $R^6$, which may be the same or different, represent hydrogen atoms or aliphatic or cycloaliphatic groups; and especially where $R^4$ represents a group of the formula

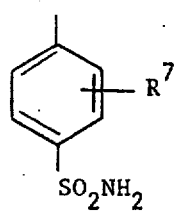

II in which $R^7$ represents a hydrogen, fluorine, chlorine or bromine atom or a lower alkyl or trifluoromethyl group and where $R^5$ and $R^6$ are hydrogen atoms or lower alkyl or aycloalkyl groups.

$R^1$, when aryl, may be unsubstituted or may carry substituents such as alkoxy groups, e.g. methoxy groups, lower alkyl groups e.g. methyl, ethyl, propyl or amyl groups or halogen atoms. The phenyl group is preferred. When $R^1$ is a cycloaliphatic group it is preferably a cycloalkyl or cycloalkenyl group having 5–10 carbon atoms, e.g. a cyclopentyl, cyclohexyl, adamantyl, decalinyl or cyclohexenyl group. $R^7$ is preferably in the 2-position and in general halogen atoms, particularly chlorine or fluorine, give especially good results. Where $R^7$ is a lower alkyl group, it preferably has 1–6 carbon atoms; the methyl group is especially preferred.

As mentioned above, the compounds according to the present invention show interesting activity against both Grand Mal and Petit Mal forms of epilepsy. This activity is indicated respectively by the electro shock test and the Cardiazol shock test. It is noteworthy that the toxicity of the compounds in which $R^2$ and $R^3$ represent an oxo group is markedly less than that of corresponding hydantoins having no sulphamoylphenyl group and, indeed, all the compounds are characterised by possessing very high $LD_{50}$ values, often greater than 7500 mg/kg. Activity and toxicity for some particularly noteworthy compounds are shown in the following table.

| Product of Example No. | Toxicity $LD_{50}$ mg/kg | Electro shock $ED_{50}$ mg/kg (mouse) | $ED_{50}$ mg/kg (rat) | Cardiazol shock $ED_{50}$ mg/kg (mouse) |
|---|---|---|---|---|
| 2 | 7500 | 10 | 10 | 50 |
| 3 | 7000 | 5 | 1 | 50 |
| 5 | 7500 | 5–10 | 5 | 50 |
| 8 | 7000 | 10 | 5 | 100 |
| 18 | — | 10 | — | 50 |
| 19 | — | 25 | 10 | 200 |

It will be noted that the ratio of $ED_{50}/LD_{50}$ for the compounds according to the invention is particularly favourable. The compound 1-phenyl-3-(2-chloro-4-sulphamoylphenyl)-imidazolidin-4-one showed virtually no sedative activity up to 500 mg/kg.

Other compounds according to the invention have similar properties; such products include:

1-phenyl-3-p-sulphamoylphenyl-imidazolidin-4-one;

1-phenyl-3-(3-chloro-4-sulphamoylphenyl)-imidazolidin-4-one;

1-phenyl-3-(2-methyl-4-sulphamoylphenyl)-imidazolidin-4-one;

1-phenyl-3-(2-trifluoromethyl-4-sulphamoylphenyl)-imidazolidin-4-one; and 1-cyclohexyl-3-(2-chloro-4-sulphamoylphenyl)-imidazolidin-4-one.

According to a further feature of the invention there are provided pharmaceutical compositions containing one or more compounds according to the invention together with one or more pharmaceutical carriers or excipients.

Thus, for example, the compositions may take the form of tablets, coated tablets, capsules, lozenges, suppositories, ampoules for injection or solutions.

The carriers or excipients in such compositions may, for example be those conventional for such forms and may include starch, lactose, magnesium stearate, talc, gelatin, sterile pyrogen-free water, or suspending, emulsifying, dispersing, thickening or flavouring agents.

Dosage units forms such as tablets, capsules, suppositories or ampoules are preferred and advantageously each unit contains 10 to 1000 mg. of active substances, preferably 100 to 300 mg.

The compositions, preferably contain the active substance at a concentration from 0.10 to 80.0% by weight.

According to a still further feature of the invention there is provided a process for the preparation of the novel compounds of this invention a compound of the general formula

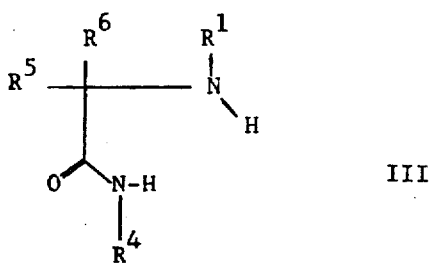

III (where $R^1$, $R^5$ and $R^6$ are as defined for formula I) is reacted with a carbonyl derivative of the formula

VI where X and Y represent hydrogen atoms or X and Y which may be the same or different represent halogen atoms or alkoxy groups; or with an ortho- or pyroester of a carbonyl derivative of formula VI in which X and Y both represent alkoxy groups. That is to say (a) the compound of general formula III is reacted with formaldehyde (or a polymeric form thereof) to give a compound of formula I in which $R^2$ and $R^3$ represent hydrogen atoms; or (b) the compound of formula III is reacted with a reactive derivative of carbonic acid to give in one or more stages a compound of the formula I in which $R^2$ and $R^3$ represent an oxo group.

In particular there is provided a process in which a compound of formula III is used in which $R^1$ represents an aryl group or cycloaliphatic group and $R^4$ represents a phenyl group, one of $R^1$ and $R^4$ representing a sulphamoylphenyl group, especially a compound where $R^4$ represents a group of the formula

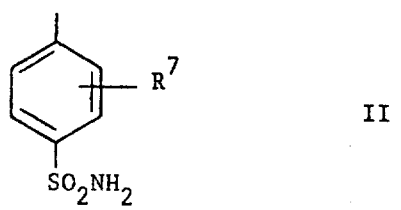

II where $R^7$ represents a hydrogen, fluorine, chlorine or bromine atom or a lower alkyl or trifluoromethyl group.

The compound of formula III preferably as $R^5$ and $R^6$ representing hydrogen atoms, or lower alkyl or cycloalkyl groups. $R^1$ preferably represents an unsubstituted aryl group; an aryl group substituted by an alkoxy or lower alkyl group or a halogen atom; or a cycloalkyl group. $R^7$ preferably represents a fluorine or chlorine atom or a methyl group in the 2-position relative to the imidazolidinone ring.

The reaction with formaldehyde is conveniently effected in an inert polar solvent, preferably of high dielectric constant, for example a lower alkanol, e.g. methanol or ethanol; a dialkylamide e.g. dimethylformamide or dimethylacetamide; an ether, e.g. dioxane, T.H.F. or cellosolve; a dialkylsuphoxide, e.g. dimethylsulphoxide; nitrobenzene or water; or a mixture thereof. The reaction is preferably effected at an elevated temperature, e.g. at the reflux temperature of the reaction medium. In general a temperature of from 50° to 150°, especially 80°-100°, is suitable.

The derivative of carbonic acid is preferably a lower alkyl chloroformate. The reaction is preferably effected at an elevated temperature either at reflux or in an autoclave at higher temperatures, e.g. up to 150°C. In milder circumstances there may be obtained an intermediate of formula

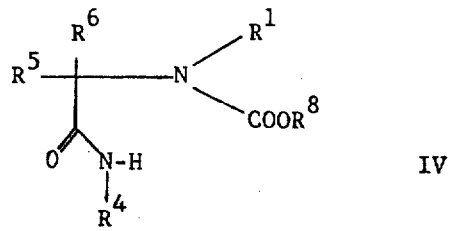

IV (in which $R^1$, $R^7$, $R^5$ and $R^6$ are as defined above and $R^8$ represents a lower alkyl group), the reaction being effected preferably in an excess of chloroformate at an elevated temperature. The intermediate of formula IV may then be hydrolysed to give the corresponding N-carboxyl compound which may then be cyclised, e.g. at a moderately elevated temperature. Alternatively, the compound of formula III may be cyclised directly in one stage by using more vigorous conditions.

The α-aminoacetamide starting material, i.e. the compound of formula III, may be prepared by reaction of an amine with a correspondng α-halogeno-N-substituted-acetamide. For example, an arylamine such as aniline may be reacted with a 2-chloro-N-(4-sulphamoylphenyl)-acetamide. A base is desirably present to bind the hydrogen chloride evolved, and this is conveniently an excess of the arylamine. The α-halogenoacetamide is conveniently prepared by reaction of an α-halogenoacetyl halide with a 4-sulphamoylaniline.

The imidazolidinone compounds according to the invention may also be prepared from corresponding compounds lacking a sulphamoyl group by reaction with reagents for introducing a sulphamoyl group. Thus, a compound of the general formula I as defined above except that one of $R^1$ and $R^4$ represents a halosulphonyl group, especially a compound of the formula

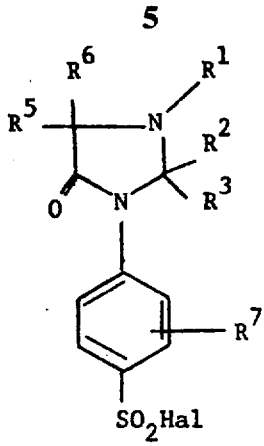

V (where $R^1$, $R^2$, $R^3$, $R^5$, $R^6$ and $R^7$ are as defined above and Hal is a halogen atom, e.g. chlorine) may be reacted with ammonia. The group —$SO_2Hal$ may be introduced, for example, by diazotisation of the corresponding amine of general formula

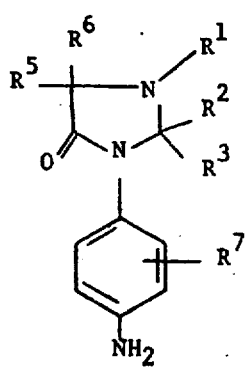

VI (where $R^1$, $R^2$, $R^3$, $R^5$, $R^6$ and $R^7$ are as defined above) and treatment with sulphur dioxide in the presence of a cupric halide. The amide of formula V can be prepared by reduction of the corresponding nitro compound which in turn may be prepared by reaction similar to that of the intermediate of formula II using the required 4-nitro analogue.

The following examples further illustrate the invention. All temperatures are in °C; melting points are given for samples recrystallised from ethyl acetate unless otherwise stated.

EXAMPLE 1

1-Phenyl-3-(p-sulphamoylphenyl)-imidazolidin-4-one a. α-Chloro-4-sulphamoylacetanilide Sulphanilamide (17.2g) and α-chloroacetyl chloride (7.55 ml) were refluxed together for 1 hour, cooled, ground in a mortar with ice/water and filtered to give 26.5 g of the title compound. Recrystallisation from ethanol gave m.p. 215°–219°.

$C_8H_9ClN_2O_3S$ (248.69) Requires: C, 38.64; H, 3.64; N, 11.26%. Found: C, 38.57; H, 3.65; N, 11.30%.

b. α-Phenylamino-4-sulphamoyl acetanilide

α-Chloro-4-sulphamoylacetanilide (24.9g) and aniline (18.6g) were heated together on a water bath (90°) for 30 min. The mixture was added to ethyl acetate and water and shaken. The product was isolated by evaporation to give 13.0 g; m.p. 192 – 193.

$C_{14}H_{15}N_3O_3S$ (305.36) Requires: C, 55.13; H, 4.96; N, 13.78%. Found: C, 54.98; H, 4.96; N, 13.71%.

c. 1-Phenyl-3-(p-sulphamoylphenyl)-imidazolidin-4-one

α-Phenylamino-4-sulphamoylacetanilide (15.2g) was dissolved in ethanol (200 ml) and paraformaldehyde (1.8g) in water (400 ml) added thereto. The mixture was refluxed for 4 hours, cooled and filtered to yield 8g of the title compound. M.p. 252°–254° (acetone)

$C_{15}H_{15}N_3O_3S$ (317.37) Requires: C, 56.83; H, 4.7; N, 13.26%. Found: C, 56.74; H, 4.86; N, 13.14%.

EXAMPLE 2

1-Phenyl-3-(2-fluoro-4-sulphamoylphenyl)-imidazolidin-4-one a. 2-Chloro-N-(2-fluoro-4-sulphamoylphenyl)-acetamide 2-Fluoro-4-sulphamoyl-aniline (7.6g) and α-chloroacetyl chloride (12.0g) were refluxed together for 60 min. The reaction product was ground in a mortar with ice/water and filtered (8.3g). Recrystallisation from ethyl acetate to give beige needles m.p. 185°–187°

$C_8H_8ClFN_2O_3S$ (266.7) Requires: C, 36.0 H, 3.10 N, 10.5%. Found: C, 36.07 H, 3.12 N, 10.48%.

b. 2-Phenylamino-N-(2-fluoro-4-sulphamoylphenyl)-acetamide

2-Chloro-N-(2-fluoro-4-sulphamoylphenyl)-acetamide (21.0g) and aniline (17.6g) were heated together on a water bath (90°) for 60 min. The product was worked up as in Example 1 (b) to yield 29g, m.p. 197°–198°C $C_{14}H_{14}FN_3O_3S$ (323.34) Requires: C, 52.45 H, 4.34 N, 13.00%. Found: C, 52.02 H, 4.44 N, 12.92%.

c. 1-Phenyl-3-(2-fluoro-4-sulphamoylphenyl)-imidazolidin-4-one

2-Phenylamino-N-(2-fluoro-4-sulphamoylphenyl)-acetamide (9.6g) was dissolved in ethanol (140 ml) and paraformaldehyde (1.5g) in water (285 ml) added. The mixture was refluxed 4 hours, cooled and filtered to yield the title product (3g), m.p. 210°–213°

$C_{15}H_{14}FN_3O_3S$ (335.35) Requires: C, 53.68; H, 4.22; N, 12.6%. Found: C, 53.54; H, 4.32; N, 12.29%.

EXAMPLE 3

1-Phenyl-3-(2-Chloro-4-sulphamoylphenyl)-imidazolidin-4-one a. 2-Chloro-N-(2-chloro-4-sulphamoylphenyl)-acetamide 2-Chloro-4-sulphamoylaniline (50 g) and α-chloroacetyl chloride (24 ml) were refluxed together for 45 min. and the product worked up as in Example 2(a) to yield 59.5 g, m.p. 162°–164°

$C_8H_8Cl_2N_2O_3S$ (283.15) Requires: C, 33.95; H, 2.84; N, 9.90; S, 11.33 Cl, 25.06% Found: C, 33.72; H, 2.88; N, 9.89; S, 11.28; Cl, 25.08% b. 2-Phenylamino-N-(2-chloro-4-sulphamoylphenyl)-acetamide

2-Chloro-N-(2-chloro-4-sulphamoylphenyl)-acetamide (28.3g 0.1 mole) and aniline (18.6g, 0.2 mole) were heated together for 30 min. on a water bath (90°). The mixture was worked up as in Example 1(b) to yield 20.8 g m.p. 185°–186°

$C_{14}H_{14}ClN_3O_3S$ (339.81) Requires: C: 49.45; H, 3.85; N, 12.36%. Found: C: 49.47; H, 4.10; N, 12.42%.

c. 1-Phenyl-3-(2-chloro-4-sulphamoylphenyl)-imidazolidine-4-one

2-Phenylamino-N-(2-chloro-4-sulphamoylphenyl)-acetamide (34.0g) was dissolved in ethanol (300 ml) and paraformaldehyde (6.0g) in water (600 ml) added. The mixture was refluxed 4 hours, cooled and worked up as in Example 2(c) to yield 20 g m.p. 206°

$C_{15}H_{14}ClN_3O_3S$ (350.82) Requires: C: 51,32 H: 3,72 N: 11,97%. Found: C: 51,28 H: 3,84 N: 11,87%.

EXAMPLE 4

1-Phenyl-3-(3-chloro-4-sulphamoylphenyl)-imidazolidine-4-one a. 2-Chloro-N-(3-chloro-4-sulphamoylphenyl)-acetamide 3-Chloro-4-sulphamoylaniline (20.6 g) and chloroacetyl chloride (20 ml) were refluxed 45 min and the mixture worked up as in Example 2(a) to yield 23.5 g m.p.: 214°–216°.

$C_8H_8Cl_2N_2O_3S$ (283,15) Requires: C: 33,95 H: 2,84 N: 9,90%. Found: C: 33,97 H: 2,88 N: 10.00%.

b. 2-Phenylamino-N-(3-chloro-4-sulphamoylphenyl)-acetamide

2-Chloro-N-(3-chloro-4-sulphamoylphenyl)-acetamide (28.3 g) and aniline (19 ml) were heated together for 30 min on a water bath (90°) and the product worked up as in Example 1(b) to yield 25 g, m.p. 192°–194°.

$C_{14}H_{14}ClN_3O_3S$ (339,8) Requires: C: 49,45 H: 3,85 N: 12,36%. Found: C: 49,39 H: 4,13 N: 12,38%.

c. 1-Phenyl-3-(3-chloro-4-sulphamoylphenyl)-imidazolidin-4-one

2-Phenylamino-N-(3-chloro-4-sulphamoylphenyl)-acetamide (34 g) was dissolved in ethanol (300 ml) and paraformaldehyde (6.0 g) in water (600 ml) added. The mixture was refluxed 4 hrs and cooled. The product was worked up as in Example 1(c) to yield: 18 g, m.p. 257°–259°.

$C_{15}H_{14}ClN_3O_3S$ (351,8) Requires: C: 51,18 H: 4,01 N: 11,94%. Found: C: 51,25 H: 3,93 N: 11,92%.

EXAMPLE 5

1-Phenyl-3-(2-bromo-4-sulphamoylphenyl)imidazolidin-4-one a. 2-Chloro-N-(2-bromo-4-sulphamoylphenyl)-acetamide 2-Bromo-4-sulphamoylaniline (20.0 g) and α-chloroacetyl chloride (25.0 g) were refluxed together for 60 min. and the product worked up as in Example 2(a) to yield 20.5 g white needles, m.p. 174°–175°

$C_8H_8BrClN_2O_3S$ (327,57) Requires: C: 29,4 H: 2,46 N: 8,57%. Found: C: 29,49 H: 2,55 N: 8,67%.

b. 2-Phenylamino-N-(2-bromo-4-sulphamoylphenyl)-acetamide

2-Chloro-N-(2-bromo-4-sulphamoylphenyl)-acetamide (16.4g) and aniline (9.0 g) were heated together for 60 min. on a water bath at 90° the product was worked up as in Example 1(b) to yield 15,5 g beige crystals m.p.: 179°–181°.

$C_{14}H_{14}BrN_3O_3S$ (384.25) Requires: C: 43.68 H: 3,67 N: 10,9%. Found: C: 43.72 H: 3,70 N: 10,90%.

c. 1-Phenyl-3-(2-bromo-4-sulphamoylphenyl)-imidazolidine-4-one

2-Phenylamino-N-(2-bromo-4-sulphomaoylphenyl)-acetamide (19.2 g) was dissolved in ethanol (200 mg) and paraformaldehyde (2.2 g) in water (420 ml) added. The mixture was refluxed for 2 hr and cooled. The product was then worked up as in Example 2(c) to yield 9.3 g m.p.: 193°–200°

$C_{15}H_{14}BrN_3O_3S$ (396.26) Requires: C: 45,48 H: 3,56 N: 10,62%. Found: C: 45,42 H: 3,67 N: 10,61%.

EXAMPLE 6

1-Phenyl-3-(2-methyl-4-sulphamoylphenyl)-imidazolidin-4-one a. 2-Chloro-N-(2-methyl-4-sulphamoylphenyl)-acetamide 2-methyl-4-sulphamoylaniline (18,6 g) and α-chloroacetyl chloride (30g) were refluxed together 30 min. and the mixture worked up as in Example 2(a) to yield 11 g, m.p. 193°–194°

$C_9H_{11}ClN_2O_3S$ (262,7) Requires: C: 41,14 H: 4,22 N: 10,66%. Found: C: 41,23 H: 4,30 N: 10,65%.

b. 2-Phenylamino-N-(2-methyl-4-sulphamoylphenyl)-acetamide

2-Chloro-N-(2-methyl-4-sulphamoylphenyl)-acetamide (13.1g) and aniline (9.5 g) were heated together 2½ hr on a water bath at 90°. The mixture was worked up as in Example 1(b) to yield 7 g beige crystals, m.p. 195°–196°

$C_{15}H_{17}N_3O_3S$ (319.3) Requires: C: 56,40 H: 5,37 N: 13,15%. Found: C: 56,45 H: 5,46 N: 13.09%.

c. 1-Phenyl-3-(2-methyl-4-sulphamoylphenyl)-imidazolidin-4-one

2-Phenylamino-N-(2-methyl-4-sulphamoylphenyl)-acetamide (16 g) was dissolved in ethano, (320 ml) and paraformaldehyde (1.9 g) in water (640 ml) added. The mixture was refluxed 1½ hr, cooled and filtered.

The residue was crystallised from DMF/water to yield 16 g, m.p. 206°–210°.

$C_{16}H_{17}N_3O_3S$ (331.4) Requires: C: 58,05 H: 5,18 N: 12,70 S: 9,69%. Found: C: 56,98 H: 5,16 N: 12,52 S: 9,58%.

EXAMPLE 7

1-Phenyl-3-(3-trifluoromethyl-4-sulphamoylphenyl)-imidazolidin-4-one a. 2-Chloro-N-(3-trifluoromethyl-4-sulphamoylphenyl)-acetamide 3-Trifluoromethyl-4-sulphamoylaniline (24.0g) and α-chloroacetyl chloride (20 ml) were refluxed together 30 mins and the mixture worked up as in Example 2(a) to yield 28 g, m.p. 185°–190°

$C_9H_8ClF_3N_2O_3S$ (316.7)
Requires: C: 34,10 H: 2,55 N: 8,85%
Found: C: 34,23 H: 2,64 N: 8,77% b. 2-Phenylamino-N-(3-trifluoromethyl-4-sulphamoylphenyl)-acetamide

2-Chloro-N-(3-trifluoromethyl-4-sulphamoylphenyl)-acetamide (31.7g) aniline (19g) were heated together 40 min. at 120°–130°C and the mixture worked up as in Example 1(b) to yield 18 g, m.p. 172°

$C_{15}H_{14}F_3N_3O_3S$ (373.4)
Requires: C: 48,20 H: 3,75 N: 11,30%.
Found: C: 48,26 H: 3,82 N: 11,24%.

c. 1-Phenyl-3-(3-trifluormethyl-4-sulphamoylphenyl)-imidazolidin-4-one

2-Phenylamino-N-(3-trifluoromethyl-4-sulphamoylphenyl)-acetamide (11.2g) was added to ethanol (200 ml) and paraformaldehyde (1.3g) in water (400 ml) added thereto under reflux. The mixture was refluxed 1½ hr, cooled and worked up as in Example 6(c) to yield 11,8 g, m.p. 235°–238°.

$C_{16}H_{14}F_3N_3O_3S$ (385.4)
Requires: C: 49,91 H: 3,67 N: 10,92%.
Found: C: 49,57 H: 3.77 N: 10,51%.

EXAMPLE 8

1-Phenyl-3-(2-chloro-4-sulphamoylphenyl)-hydantoin a. 2-(N-methoxycarbonyl-phenylamino)-N-(2-chloro-4-sulphamoylphenyl)-acetamide 2-Phenylamino-N-(2-chloro-4-sulphanoylphenyl)-acetamide (11.3g) and methyl chloroformate (32.6 ml) were heated together for 30 min. at 100°. The excess methyl chloroformate was then distilled off and the mixture worked up as in Example 2(a) to yield 8.7 g white cryatals, m.p.: 196°–198°.

$C_{16}H_{16}ClN_3O_5S$ (397.85)
Requires: C: 48,28 H: 4,05 N: 10,56%.
Found: C: 48,22 H: 4,04 N: 10,56%.

b. 2-(N-carboxy-phenylamino)-N-(2-chloro-4-sulphamoylphenyl)-acetamide 2-(N-methoxycarbonyl-phenylamino)-N-(2-chloro-4-sulphamoyl phenyl)-acetamide (15 g) was dissolved in 50% aqueous KOH (40 ml).

The mixture was then cooled and acidified with conc. HCl. The mixture was then heated on a water bath for a short while, filtered and the residue liberally washed with water to yield 11.0 g. Recrystallisation from ethyl acetate gave m.p. 179°–182°.

$C_{15}H_{14}ClN_3O_5S$ (383.8)
Requires: C: 46,91 H: 3,68 N: 10,94%.
Found: C: 46,80 H: 3,71 N: 10,87%.

c. 1-Phenyl-3-(2-chloro-4-sulphamoylphenyl)-hydantoin 2-(N-carboxy-phenylamino)-N-(2-chloro-4-sulphamoylphenyl)-acetamide (5.0 g) was heated in acetic anhydride (20 ml) 2 hr at 80°. The anhydride was then distilled off and the residue digested with water, filtered off and further washed with water to yield 3.5 g, m.p. 241°–243° on recrystallisation from ethyl acetate.

$C_{15}H_{12}ClN_3O_4S$ (365.8)
Requires: C: 49,22 H: 3,30 N: 11,48%.
Found: C: 49,04 H: 3,41 N: 11,32%.

EXAMPLE 9

1-Cyclohexyl-3-(2-chloro-4-sulphamoylphenyl)-imidazolidin-4-one a. 2-Cyclohexylamino-N-(2-chloro-4-sulphamoylphenyl)-acetamide 2-Chloro-N-(2-chloro-4-sulphamoylphenyl)-acetamide (28.3g) and cyclohexylamine (19.8 g) were heated together 30 min. on a water bath at 90°. The mixture was then treated with ethyl acetate and water and the product extracted with ethyl acetate. A yield of 25g was obtained; m.p. 213°–215° from ethanol.

$C_{14}H_{20}ClN_3O_3S$ (345.86) Requires: C: 48,60 H: 5.83 N: 12.15% Found: C: 48,44 H: 5.86 N: 12.00% b. 1-Cyclohexyl-3-(2-chloro-4-sulphamoylphenyl)-imidazolidin-4-one

2-Cyclohexylamino-N-(2-chloro-4-sulphamoylphenyl)-acetamide (17.2g) was dissolved in ethanol (150 ml) and paraformaldehyde (3g) in water (300 ml) added. The mixture was refluxed 2 hrs, cooled and filtered. The residue was crystallised from ethanol/petroleum ether. Yield 13.5 g, m.p. 188°–190°.

$C_{15}H_{20}ClN_3O_3S$ (357.84) Requires: C: 50.32 H: 5.63 N: 11.74%. Found: C: 50.28 H: 5.65 N: 11.68%.

EXAMPLE 10

1-(p-Chlorophenyl)-3-(2-chloro-4-sulphamoylphenyl)-imidazolidin-4-one a. 2-(p-Chloroanilino)-N-(2-chloro-4-sulphamoylphenyl)-acetamide 2-Chloro-N-(2-chloro-4-sulphamoylphenyl)-acetamide (7g) and p-chloroaniline (6.3 g) were heated together for 45 minutes on a water bath at 90°. The mixture was worked up as in Example 1(b) to yield the title product (4.5 g), m.p. 185°.

$C_{14}H_{13}Cl_2N_3O_3S$ 374.3
Requires: C: 44.96; N: 3.50; N: 11.24%.
Found: C: 44.84; H: 3.52; N: 11.31%.

b. 1-(p-Chlorophenyl)-3-(2-chloro-4-sulphamoylphenyl)-imidazolidin-4-one 2-(p-Chloroanilino)-N-(2-chloro-4-sulphamoylphenyl)-acetamide (3g) was dissolved in ethanol (40 ml) and paraformaldehyde (0.5g) in water (80 ml) added thereto. The mixture was refluxed for 3 hours, cooled and filtered to yield the title product (2.1g), m.p. 222°–225°(ethanol).

$C_{15}H_{13}Cl_2N_3O_3S$ (386.3)
Requires: C, 46.67; H, 3.39; N, 10.89%.
Found: C, 46.66; H, 3.48; N, 10.71%.

EXAMPLE 11

1-(p-Methylphenyl)-3-(2-chloro-4-sulphamoylphenyl)-imidazolidin-4-one a. 2-(p-Methylanilino)-N-(2-chloro-4sulphamoylphenyl)-acetamide 2-Chloro-N-(2-chloro-4-sulphamoylphenyl)-acetamide (28.3g) and p-toluidine (21.4g) were heated together for 45 minutes on a water bath at 90°. The mixture was worked up as in Example 1(b) to yield the title compound (43g), m.p. 215°–216°

$C_{15}H_{16}ClN_3O_3S$ (353.84)

Requires: C, 50.89 H, 4.56 N, 11.87%
Found: C, 50.89 H, 4.66 N, 11.77% b. 1-(p-Methylphenyl)-3-(2-chloro-4-sulphamoylphenyl)-imidazolidin-4-one 2-(p-Methylanilino)-N-(2-chloro-4-sulphamoylphenyl)-acetamide (15g) was dissolved in ethanol (200 ml) and paraformaldehyde (2.5 g) in water (400ml) added thereto. The mixture was refluxed for 3 hours, cooled in ice/water and filtered to yield the title compound (6.45g), m.p. 223°–226° (ethanol).

$C_{16}H_{16}ClN_3O_3S$ (265.85)

Requires: C, 52.50; H, 4.41; N, 11.48%.
Found: C, 52.52; H, 4.45; N, 11.46%.

EXAMPLE 12

1-(p-Methoxyphenyl)-3-(2-chloro-4-sulphamoylphenyl)-imidazolidin-4-one a. 2-(p-Methoxyanilino)-N-(2-chloro-4-sulphamoylphenyl)-acetamide 2-Chloro-N-(2-chloro-4-sulphamoylphenyl)-acetamide (7g) and p-anisidine (6.2g) were heated together for 45 minutes on a water bath (90°). The mixture was worked up as in Example 1 to yield the title compound (5g), m.p. 152°–154°C (acetone).

$C_{15}H_{16}ClN_3O_4S$ (369.84).

Requires: C, 48.69; H, 4.36; N, 11.36%
Found: C, 48.70; H, 4.44; N, 11.26% b. 1-(p-Methoxyphenyl)-3-(2-chloro-4-sulphamoylphenyl)-imidazolidin-4-one

The product of stage a) (15g) was dissolved in ethanol (200 ml) and treated with paraformaldehyde (2.5g) in water (400 ml). The mixture was refluxed for 3 hours, cooled in ice/water and filtered to yield the title product (5 g), m.p. 221°–223°

$C_{16}H_{16}ClN_3O_4S$ (381.84)

Requires: C, 50.30; H, 4.22; N, 11.00%.
Found: C, 50.25; H, 4.30; N, 10.95%.

EXAMPLE 13

1-Phenyl-3-(2-chloro-4-sulphamoylphenyl)-imidazolidin-4-one

2-Phenylamino-N-(2-chloro-4-sulphamoylphenyl)-acetamide (0.8g) was dissolved in dimethylformamide (20ml) and paraformaldehyde (100 g) in water (5 ml) added thereto. The mixture was kept at 80° for 24 hours and then the DMF was evaporated. The residue was recrystallised from ethanol to yield the product (500 mg.), m.p. 204°; mixed melting point with the product of Example 3(c) 206°. The product was found identical with the product of Example 3(c) on thin layer chromatography (Kieselgel F254, Merck; benzene; methanol 16:1) and on IR spectroscopy.

EXAMPLE 14

1-Cyclohexyl-3-(4-sulphamoylphenyl)-imidazolidin-4-one a. 2-Chloro-N-(4-nitrophenyl)-acetamide p-Nitroaniline (10.0g) and chloroacetyl chloride (15 ml) were refluxed together 1 hour, mixed with ethyl acetate and washed with water 3 times to yield 11.5 g; mp 183°–185°C.

$C_8H_7ClN_2O_3$ (214.63)

Req. C: 44.69 H: 3.28 N: 13.03%.
Found: C: 44.65 H: 3.36 N: 13.08%.

b. 2-Cyclohexylamino-N-(4-nitrophenyl)-acetamide

2-Chloro-N-(4-nitrophenyl)-acetamide (11.5g) and cyclohexylamine (10.7g) were heated together 2 hours at 150° and then added to ethyl acetate/water. The product was extracted with ethyl acetate to yield 9.0g, m.p. 123°–125°C.

$C_{14}H_{19}N_3O_3$ (277.32)

Req. C: 60.63 H: 6.91 N: 15.15%.
Found: C: 60.55 H: 6.93 N: 15.12%.

c. 1-Cyclohexyl-3-(4-nitrophenyl)-imidazolidin-4-one

2-Cyclohexylamino-N-(4-nitrophenyl)-acetamide (3.5g) were added to ethanol (85 ml). p-Formaldehyde (0.8g) in water (110 ml) was added and the mixture was refluxed 4 hours, cooled and filtered to yield 3.1 g, m.p. 132°–133°C $C_{15}H_{19}N_3O_3$ (289.33) Req: C: 62.26 H: 6.62 N: 14.52% Found: C: 62.19 H: 6.67 N: 14.59% d. 1-Cyclohexyl-3-(4-aminophenyl)-imidazolidin-4-one

1-Cyclohexyl-3-(4-nitrophenyl)-imidazolidin-4-one (2.9g) was dissolved in ethanol (500 ml) and 200 mg Raney nickel added. The mixture was then hydrogenated.

$H_2$-Uptake: Theory:710 ml Actual: 730 ml
Yield: 1.8g, m.p.: 145-146°C $C_{15}H_{21}N_3O$ (259.4) Req: C: 69.46 H: 8.16 N: 16.21%. Found: C: 69.46 H: 8.16 N: 16.19%.

e. 1-Cyclohexyl-3-(4-sulphamoylphenyl)-imidazolidin-4-one

1-Cyclohexyl-3-(4-aminophenyl)-imidazolidin-4-one (10.4g) was dissolved in glacial acetic acid (44.0 ml) and conc. HCL (72.0 ml). At 0°–5°C there was added with stirring NaNO$_2$ (38g) in water (17.2 ml). The diazonium solution so obtained was added to a solution of CuCl$_2$ (2.4 ml –50%) in glacial acetic acid (84.0 ml) saturated at 0°C with SO$_2$. The mixture was stirred a further 15 minutes and then poured into water (250 ml). The precipitate was filtered off and added to conc. ammonia (150 ml). The mixture was heated and then filtered to yield 4.8 g, m.p. 190°–193°C (ethanol)

$C_{15}H_{21}N_3O_3S$ (323.43) Req: C: 55.77 H: 6.55 N: 13.01%. Found: C: 55.64 H: 6.54 N: 12.95%.

15.

1-(3-Methoxyphenyl)-3-(2-chloro-4-sulphamoylphenyl)-imidazolidin-4-one a. 2-(3-Methoxyanilino)-N-(2-chloro-4-sulphamoylphenyl)-acetamide 2-Chloro-4-(chloro-4-sulphamoylphenyl)-acetamide (28.3g) and m-anisidine (31.8g) were heated together on an oil bath for 7 hours at 175°–180°C. The mixture was then mixed with ethylacetate/water and extracted to yield 17.2 g, m.p. 148°–152°C (ethanol).

$C_{15}H_{16}ClN_3O_4S$ (369.8) Req. C: 48.69 H: 4.36 N: 11.36%. Found: C: 48.76 H: 4.42 N: 11.36%.

b. 1-(3-Methoxyphenyl)-3-(2-chloro-4-sulphamoylphenyl)-imidazolidin-4-one 2-(3-Methoxyanilino)-N-2-chloro-4-sulphamoylphenyl)-acetamide(18.5 g) was dissolved in ethanol (250 ml) and to the solution was added p-formaldehyde (3.0 g) in water (500 ml). The mixture was refluxed for 4 hours, cooled and filtered to yield 16.2 g product, m.p. 200°–203°C (ethanol).

$C_{16}H_{16}ClN_3O_4S$ (381.9) Req: C: 50.20 H: 4.22 N: 11.01%. Found: C: 50.32 H: 4.32 N: 11.06%.

16.
1-(3-Methylphenyl)-3-(2-chloro-4-sulphamoyl-phenyl)-imidazolidin-4-one a. 2-(3-Methylanilino)-N-(2-chloro-4-sulphamoyl-phenyl)-acetamide 2-Chloro-N-(2-chloro-4-sulphamoylphenyl)-acetamide (28.3 g) and m-toluidine (31.8 g) were heated 7 hours at 175°C (oil bath) and worked up as in Example 15 to yield 22.4 g product, m.p. 185°–189°C (ethanol).

$C_{15}H_{16}ClN_3O_3S$ (353.8) Req: C: 50.89 H: 4.56 N: 11.87%. Found: C: 50.94 H: 4.65 N: 11.80%.

b.
1-(3-Methylphenyl)-3-(2-chloro-4-sulphamoyl-phenyl)-imidazolidin-4-one 2-(3-Methylanilino)-N-(2-chloro-4-sulphamoyl-phenyl)-acetamide 3.5 g dissolved in ethanol (100 ml) was reacted with p-formaldehyde (0.6 g) in water (200 ml) as in Example 15 (b) to yield 2.8 g product, m.p. 198°–202°C $C_{16}H_{16}ClN_3O_3S$ (365.85) Req: C: 52.60 H: 4.44 N: 11.50%. Found: C: 52.40 H: 4.48 N: 11.59%.

17.
1-(3-chlorophenyl)-3-(2-chloro-4-sulphamoylphenyl)-imidazolidin-4-one a. 2-(3-Chloroanilino)-N-(2-chloro-4-sulphamoyl-phenyl)-acetamide 2-Chloro-N-(2-chloro-4-sulphamoylphenyl)-acetamide was prepared from (14.0 g) and m-chloraniline (16.2 g) by heating for 5 hours at 170°C (oil bath). Work up as before gave 11.4 g product, m.p. 209 - 211°C (ethanol)

$C_{14}H_{13}Cl_2N_3O_3S$ (374.3) Req: C: 44.96 H: 3.50 N: 11.24%. Found: C: 44.97 H: 3.61 N: 11.16%.

b. 1-(3-Chlorophenyl)-3-(2-chloro-4-sulphamoyl-phenyl)-imidazolidin-4-one 2-(3-Chloroanilino)-N-(2-chloro-4-sulphamoyl-phenyl)-acetamide (18.5 g) were dissolved in ethanol and reacted with paraformaldehyde as before (3.0g) to yield 14.0 g, m.p. 208°–216°C (ethanol).

$C_{15}H_{13}Cl_2N_3O_3S$ (386.3) Req: C: 46.67 H: 3.39 N: 10.89%. Found: C: 47.45 H: 3.57 N: 10.95%.

18.
5-Methyl-1-phenyl-3-(2-chloro-4-sulphamoylphenyl)-imidazolidin-4-one a. 2-Bromo-N-(2-chloro-4-sulphamoylphenyl)-propionamide 2-Chloro-4-sulphamoylaniline (4.1 g) and α-bromopropionyl bromide (4.3 g) were heated for 30 min. at 190°C (oil bath) to yield 3.2 g, m.p. 172°–174°C.

$C_9H_{10}BrIN_2O_3S$ (341.6) Req: C: 31.61 H: 2.96 N: 8.19%. Found: C: 31.73 H: 2.99 N: 8.22%.

b. 2-Anilino-N-(2-chloro-4-sulphamoylphenl)-propionamide

2-Bromo-N-(2-chloro-4-sulphamoylphenyl)-propionamide (17.5 g) and aniline (9.6g) were heated 20 min. at a bath temp. of 150°C. Work up as before gave 16.0 g m.p. 180°–182°C $C_{15}H_{16}ClN_3O_3S$ (353.8) Req: C: 50.89 H: 4.56 N: 11.87%. Found: C: 50.96 H: 4.63 N: 11.77%.

c. 5-Methyl-1-phenyl-3-(2-chloro-4-sulphamoyl-phenyl)-imidazolidin-4-one

2-Anilino-N-(2-chloro-4-sulfamoylphenyl)-propionamide (3.5 g) was dissolved in ethanol (100 ml) and reacted with paraformaldehyde (0.7 g) as before to yield 1.8 g, m.p. 202°C $C_{16}H_{16}ClN_3O_3S$ (365.8) Req: C: 52.50 H: 4.41 N: 11.48%. Found: C: 52.47 H: 4.46 N: 11.40%.

19.
1-Cyclohexyl-3-(2-chloro-4-sulphamoylphenyl)-imidazolidin-4-one a. 2-Cyclohexylamino-N-(2-chloro-4-sulphamoyl-phenyl)-acetamide 2-Chloro-N-(2-chloro-4-sulphamoylphenyl)-acetamide was prepared as before from (10.0 g) and cyclohexylamine (7.0 g) heated 30 min. at 80°C; yield 8.5 g, m.p. 213°–215°C (ethanol)

$C_{14}H_{20}ClN_3O_3S$ (345.9) Req. C: 48.60 H: 5.83 N: 12.15%. Found: C: 48.44 H: 5.86 N: 12.00%.

b. 1-Cyclohexyl-3-(2-chloro-4-sulphamoylphenyl)-imidazolidin-4-one

2-Cyclohexylamino-N-(2-chloro-4-sulphamoyl-phenyl)-acetamide (5.0 g) was dissolved in gelost in methanol (50 ml) and reacted as before with paraformaldehyde (0.8 g) to yield 1.0 g, m.p. 188° – 190°C (ethanol/light petroleum).

$C_{15}H_{20}ClN_3O_3S$ (357.8) Req: C: 50.32 H: 5.63 N: 11.74%. Found: C: 50.28 H: 5.65 N: 11.68%.

20. 1-(4-Sulphamoylphenyl)-3-phenylhydantoin a. 2-(4-Sulphamoylanilino)-N-phenylacetamide α-Chloracetanilide (17.0 g) and sulfanilamide (34.5 g) were heated together in an autoclave for 8 hours at 120°C. The mixture was triturated with 2N HCl and filtered to yield 27.5 g, m.p. 257°–258°C (acetone).

$C_{14}H_{15}N_3O_3S$ (305.4) Req: C: 55.13 H: 4.96 N: 13.78%. Found C: 54.90 H: 5.06 N: 13.61%.

b. 1-(4-Sulphamoylphenyl)-3-phenylhydantoin 2-(4-Sulphamoylanilino)-N-phenylacetamide (1.5 g) and methyl chloroformate (15.0 ml) were heated together for 3 hours in an autoclave at 130°C. The product was filtered off as crystals; yield 500 mg, m.p. 255° – 257°C (acetone).

$C_{15}H_{13}N_3O_4S$ (331.36) Req: C: 54.43 H: 3.96 N: 12..70% Found: C: 54.25 H: 4.09 N: 12.61%.

21. 1-Phenyl-3-(4-sulphamoylphenyl)-hydantoin a. 2-(N-Methoxycarbonyl-phenylamino)-N-(4-sulphamoyl-phenyl)-acetamide 2-Anilino-N-(4-sulphamoylphenyl)-acetamide (9.0 g) was heated with methyl chloroformate (30 ml) for 45 min. at 140°C. Work up from ethyl acetate/wate gave 7.0 g, m.p. 196° – 199°C.

$C_{16}H_{17}N_3O_5S$ (365.4) Req: C: 52.93 H: 4.72 N: 11.58%. Found: C: 52.89 H: 4.76 N: 11.48%.

b. 1-Phenyl-3-(4-sulphamoylphenyl)-hydantoin 2-(N-Methoxycarbonyl-phenylamino)-N-sulphamoylphenyl)-acetamide (6.5 g) was dissolved in 50% KOH (30 ml), warmed, cooled and mixed with conc. HCl. The mixture was stirred 30 minutes and the precipitate filtered off to yield: 5.3 g, m.p. 291°–296°C (acetone)

$C_{15}H_{13}N_3O_4S$ (331.4) Req: C: 54.43 H: 3.96 N: 12.70% Found: C: 54.34 H: 4.02 N: 12.64%

22. 1-(4-sulphamoylphenyl)-3-cyclohexylhydantoin a. 2-(4-Sulphamoylanilino)-N-cyclohexylacetamide 2-Chloro-N-cyclohexylacetamide (8.7 g) and sulfanilamide (17.2g) were heated for 30 min. at 160°C. The mixture was then added to 2N NaOH and extracted with ethyl acetate to yield 8.2 g, product, m.p. 223° - 225°C b. 2-(N-Methoxycarbonyl-4-sulphamoyl-phenylamino)-N-cyclohexylacetamide 2-(4-Sulphamoylanilino)-N-cyclohexylacetamide (3.1 g) were refluxed with methyl chloroformate for 3 hours and the mixture then evaporated. The residue was taken up in ethyl acetate/water and extracted to yield 0.6 g product, m.p. 196° - 197°C (ethanol/water)

$C_{16}H_{23}N_3O_5S$ (369.3) Req: C: 52.08 H: 6.28 N: 11.39%. Found: C: 51.89 H: 6.29 N: 11.23%.

c. 1-(4-Sulphamoylphenyl)-3-cyclohexylhydantoin 2-(N-Methoxycarbonyl-4-sulphamoylphenylamino)-N-cyclohexylacetamide (3.7 g) was dissolved in hot conc. KOH (15.0 ml). The solution was cooled and acidified with conc. HCl. The mixture was heated for 30 min. on a water bath and then filtered to yield 2.5 g product, m.p. 237° - 238°C (ethanol/water $C_{15}H_{19}N_3O_4S$ (337.4) Req: C: 53.47 H: 5.68 N: 12.47%. Found: C: 53.47 H: 5.74 N: 12.41%.

EXAMPLE 23

Coated Tablets

Coated tablets are prepared containing the following ingredients:

| | |
|---|---|
| 1-Phenol-3-2-chloro-4-sulphamoylphenyl)-imidazolidin-4-one | 200 mg |
| Silica | 125.0 mg |
| Microcrystalline cellulose | 200.0 mg |
| Lubricant (silica: magnesium stearate: talc. 10:10:80) | 18.0 mg |
| Magnesium stearate U.S.P. | 6.0 mg |
| Talc | 16.7 mg |

The active ingredient is granulated with the excipients and compressed into tablet cores. These cores are sealed with a methacrylate polymer, coated with a conventional sugar coating and wax polished.

EXAMPLE 24 CAPSULES

Conventional gelatin capsules are each filled with 1-phenyl-3-(2-chloro-4-sulphamoylphenyl)-hydantoin 100 mg mixed with conventional extenders.

I claim:

1. A compound of the formula

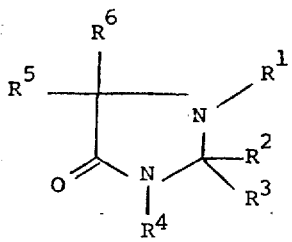

in which $R^1$ is phenyl; phenyl substituted with alkoxy, lower alkyl or halogen; or a cycloalkyl or cycloalkenyl group having 5-10 carbon atoms or a sulphamoylphenyl group, $R^4$ represents a sulphamoylphenyl or phenyl group; $R^2$ and $R^3$ each represent hydrogen atoms or an oxo group; and $R^5$ and $R^6$ are hydrogen atoms or lower alkyl or cycloalkyl groups; with the proviso that one of $R^1$ and $R^4$, but not both is a sulphamoylphenyl group.

2. A compound according to claim 1 in which $R^4$ represents a group of the formula

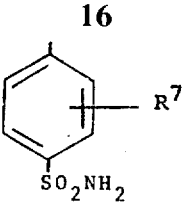

(II)

in which $R^7$ represents a hydrogen, fluorine, chlorine or bromine atom or a lower alkyl or trifluoromethyl group.

3. A compound according to claim 2 selected from the group consisting of
1-Phenyl-3-p-sulphamoylphenyl-imidazolidin-4-one;
1-phenyl-3-(2-fluoro-4-sulphamoylphenyl)-imidazolidin-4-one;
1-phenyl-3-(2-chloro-4-sulphamoylphenyl)-imidazolidin-4-one;
1-phenyl-3-(3-chloro-4-sulphamoylphenyl)-imidazolidin-4-one;
1-phenyl-3-(2-bromo-4-sulphamoylphenyl)-imidazolidin-4-one;
1-phenyl-3-(2-methyl-4-sulphamoylphenyl)-imidazolidin-4-one;
1-phenyl-3-(3-trifluoromethyl-4-sulphamoylphenyl)-imidazolidin-4-one;
1-cyclohexyl-3-(2-chloro-4-sulphamoylphenyl)-imidazolidin-4-one;
1-p-chlorophenyl-3-(2-chloro-4-sulphamoylphenyl)-imidazolidin-4-one;
1-p-methylphenyl-3-(2-chloro-4-sulphamoylphenyl)-imidazolidin-4-one;
1-p-methoxyphenyl-3-(2-chloro-4-sulphamoyl-phenyl)-imidazolidin-4-one; and
1-phenyl-3-(2-chloro-4-sulphamoylphenyl)-hydantoin.

4. A compound according to claim 2 selected from the group consisting of
1-cyclohexyl-3-p-sulphamoylphenyl-imidazolidin-4-one;
1-m-methoxyphenyl-3-(2-chloro-4-sulphamoyl-phenyl)-imidiazolidin-4-one;
1-m-methylphenyl-3-(2-chloro-4-sulphamoyl-phenyl)-imidazolidin-4-one;
1-m-chlorophenyl-3-(2-chloro-4-sulphamoyl-phenyl)-imidazolidin-4-one;
1-phenyl-3-(2-chloro-4-sulphamoylphenyl)-5-methylimidazolidin-4-one;
1-p-sulphamoylphenyl-3-phenylhydantoin; and
1-phenyl-3-p-sulphamoylphenylhydantoin.

5. A compound of the general formula

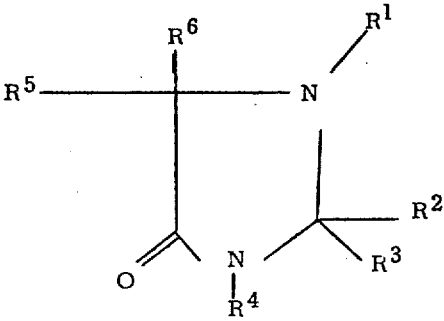

in which $R^1$ is phenyl, phenyl substituted with alkoxy, lower alkyl or halogen; or a cycloalkyl or cycloalkenyl group having 5-10 carbon atoms, $R^4$ represents a sulphamoylphenyl group; $R^2$ and $R^3$ each represent hydrogen atoms or an oxo group; and $R^5$ and $R^6$ are hydrogen atoms or lower alkyl or cycloalkyl groups.

6. A compound as claimed in claim 5, wherein $R^2$ and $R^3$ each represent a hydrogen atom.

7. A compound according to claim 5 in which $R^1$ represents a group of the formula

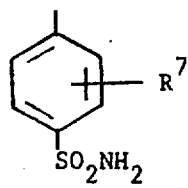

(II)

in which $R^7$ represents a hydrogen, fluorine, chlorine or bromine atom or a lower alkyl or trifluoromethyl group.

8. A compound according to claim 5 in which $R^1$ represents a phenyl group or a cyclohexyl group.

9. A compound according to claim 7 in which $R^7$ is in the 2-position relative to the imidazolidine ring.

10. A compound according to claim 9 in which $R^7$ represents a fluorine or chlorine atom or a methyl group.

11. 1-phenyl-3-(2-chloro-4-sulphamoylphenyl-)imidazolidin-4-one.

12. 1-p-sulphamoylphenyl-3-cyclohexylhydantoin.

* * * * *